United States Patent
Senegas et al.

(10) Patent No.: US 7,163,558 B2
(45) Date of Patent: Jan. 16, 2007

(54) INTERVERTEBRAL IMPLANT WITH ELASTICALLY DEFORMABLE WEDGE

(75) Inventors: Jacques Senegas, Merignac (FR); Régis Le Couedic, Andresy (FR)

(73) Assignee: Abbott Spine, Bordeaux (FR)

( * ) Notice: Subject to any disclaimer, the term of this patent is extended or adjusted under 35 U.S.C. 154(b) by 0 days.

(21) Appl. No.: 10/496,143

(22) PCT Filed: Nov. 28, 2002

(86) PCT No.: PCT/FR02/04083

§ 371 (c)(1),
(2), (4) Date: May 20, 2004

(87) PCT Pub. No.: WO03/045262

PCT Pub. Date: Jun. 5, 2003

(65) Prior Publication Data

US 2005/0004674 A1    Jan. 6, 2005

(30) Foreign Application Priority Data

Nov. 30, 2001 (FR) .................................. 01 15494

(51) Int. Cl.
*A61F 2/44* (2006.01)
(52) U.S. Cl. .................................. 623/17.11
(58) Field of Classification Search ............. 623/17.11, 623/17.12, 17.13, 17.14, 17.15, 17.16; 606/61
See application file for complete search history.

(56) References Cited

U.S. PATENT DOCUMENTS

| | | | | |
|---|---|---|---|---|
| 5,496,318 A | * | 3/1996 | Howland et al. | 606/61 |
| 5,609,634 A | * | 3/1997 | Voydeville | 623/13.11 |
| 5,725,582 A | * | 3/1998 | Bevan et al. | 606/61 |
| 6,454,806 B1 | * | 9/2002 | Cohen et al. | 623/17.15 |
| 6,468,310 B1 | * | 10/2002 | Ralph et al. | 623/17.13 |
| 6,626,943 B1 | * | 9/2003 | Eberlein et al. | 623/17.15 |
| 6,645,248 B1 | * | 11/2003 | Casutt | 623/17.12 |
| 6,673,113 B1 | * | 1/2004 | Ralph et al. | 623/17.13 |
| 6,761,720 B1 | * | 7/2004 | Senegas | 606/61 |
| 2004/0024458 A1 | * | 2/2004 | Senegas et al. | 623/17.11 |
| 2004/0106995 A1 | * | 6/2004 | Le Couedic et al. | 623/17.11 |
| 2004/0117017 A1 | * | 6/2004 | Pasquet et al. | 623/17.11 |

FOREIGN PATENT DOCUMENTS

| | | |
|---|---|---|
| DE | 28 21 678 A1 | 5/1978 |
| EP | 0322 334 A1 | 12/1988 |
| FR | 2 681 525 | 9/1991 |
| FR | 2 704 745 | 5/1993 |
| FR | 2 717 675 | 3/1994 |
| FR | 2 775 183 | 2/1998 |

* cited by examiner

*Primary Examiner*—Eduardo C. Robert
*Assistant Examiner*—Annette Reimers
(74) *Attorney, Agent, or Firm*—Cohen Pontani Lieberman & Pavane LLP

(57) ABSTRACT

An intervertebral implant comprising a spacer for engaging between two spinous processes of two vertebrae of the spine. The spacer has two elements each presenting a first part suitable for being connected to a spinous process and bearing second parts opposite from the first part, the bearing second parts being situated facing each other. An elastically-compressible member is disposed between the bearing second parts. Links are provided which are distinct from the elastically-compressible member for linking together the two elements, the link member being suitable for blocking translation movement of the two elements relative to each other when the two elements are driven apart from each other.

20 Claims, 3 Drawing Sheets

INTERVERTEBRAL IMPLANT WITH ELASTICALLY DEFORMABLE WEDGE

PRIORITY CLAIM

This is a U.S. national stage of application No. PCT/FR02/04083, filed on 28 Nov. 2002. Priority is claimed on that application and on the following application: Country: France, Application No.: 01 15494, Filed: 30 Nov. 2001.

BACKGROUND OF THE INVENTION

1. Field of the Invention

The present invention relates to an intervertebral implant including a spacer for being applied between two spinous processes of two vertebrae of the spine.

2. Discussion of Related Art

Well-known intervertebral implants comprise a spacer for inserting between the spinous processes which extend the posterior portions of vertebrae in order to limit and control relative displacement of the vertebrae relative to one another. Such implants are generally installed on the spine of a patient suffering from a degenerative pathology of the spine in which the vertebrae run the risk of approaching one another and, for example, of compressing the roots of nerves. A first category of spacers has been devised that are entirely rigid and made as a single piece presenting two opposite ends suitable for being connected respectively to two contiguous spinous processes by link means. Thus, when the spine is extended, for example, the extent to which the posterior portions of two vertebrae can move towards each other is limited by the spacer against which the spinous processes come to bear; when the spine is bent forwards, the spinous processes are held relative to each other by the link means. Nevertheless, such a rigid spacer does not reproduce accurately the real physiological conditions under which relative movement between vertebrae is limited. To mitigate that problem, a second category of spacers has been devised, made of material that is elastically deformable, thus making it possible to reproduce as accurately as possible the conditions for controlled relative displacement of vertebrae during movements of the spine. As a result, the forces tending to push vertebrae apart increase as they move towards each other.

Nevertheless, the elastically deformable materials used that are suitable for being compressed in order to limit the extent to which vertebrae can move towards each other deform in the longitudinal direction in a manner that is too great compared with the displacements of the vertebrae of a normal person.

OBJECTS AND SUMMARY OF THE INVENTION

A problem which arises and which the present invention seeks to solve is thus how to make a spacer that serves not only to control progressive movement of vertebrae towards each other in order to limit such movement, but which also make it possible to prevent the spinous processes of the vertebrae from moving too far apart when they are driven away from each other.

To this end, the present invention provides an intervertebral implant comprising a spacer, said spacer comprising: two elements each presenting a first part suitable for being connected to a spinous process and a bearing second part opposite from said first part, the bearing second parts being situated facing each other; elastically-compressible means disposed between said bearing second parts, said elastically-compressible means being suitable for being compressed by said bearing second parts when said two elements are driven towards each other; and link means distinct from the elastically-compressible means for linking together said two elements, said link means being suitable for blocking translation movement of said two elements relative to each other when said two elements are driven apart from each other.

Thus, a characteristic of the intervertebral implant of the invention lies in the way in which two elements secured to spinous processes are linked together by link means suitable for preventing said elements from moving in translation when they are moved away from each other, and by elastically-compressible means interposed between the second bearing parts which hold the elements spaced apart from each other. As a result, the spacer compresses longitudinally as the processes move towards each other, with the force that the first parts exert thereon in order to keep them apart being proportional to the extent to which the elastically-compressible means are compressed, and thus to the relative displacement of the processes relative to each other, and the spacer also prevents the processes from moving further apart from each other once the elastically-compressible means have returned to their rest state in said implant.

It will be understood that the elastically-compressible means are used only during the compression stage, and that they perform their function during this stage only. During an extension stage, they are not subjected to force, with only the link means being subjected to force, having the function of constituting a rigid block on displacement of the spinous processes in directions going apart from each other. This makes it possible to adjust separately the way in which the processes move towards each other and apart from each other.

In a particularly advantageous embodiment of the invention, said link means comprise at least one passageway passing through each of said elements and opening out substantially on either side of said bearing second part. As a result, said elements can be held with their second parts facing each other in a manner that is perfectly symmetrical on either side of said bearing part. Preferably, said link means include a loop-forming continuous link, said continuous link presenting two opposite first parts passing respectively through said two facing elements. Thus, the link is secured to the two elements in such a manner as to block them relative to each other when they move apart from each other, so that the link becomes tensioned. Advantageously, the link follows the passageway passing through said elements.

In a preferred embodiment of the invention, each of said elements presents at least a first portion and a second portion situated substantially on either side of said bearing second part, the first portion and the second portion of one of said elements being suitable for pressing respectively against the second portion and the first portion of the other element when said two elements are driven towards each other so as to block them against moving in translation relative to each other, the bearing second parts being suitable for compressing said elastically-compressible means. Thus, according to this characteristic, the compressibility of the spacer is limited by the first and second portions of the two elements. The spacer is thus capable of deforming between a rest or first position in which respectively the first and second portions of said elements are held spaced apart from each other and in which the elastically-compressible means are lightly compressed between the bearing second parts and maintain the link means extended, and a stop or second position in which the first and second portions of said elements are respectively in contact and in which the bearing second parts compress said elastically-compressible means.

Naturally, the compressibility of the elastically-compressible means, and the space between the first and second portions of said elements in said rest position need to be adjusted in such a manner that the force exerted by the elastically-compressible means on the facing bearing second parts when they are compressed is large when the first and second portions come into contact. Thus, the spacer acts effectively as a damper without it being possible for the elements to come into contact violently.

According to an advantageous characteristic, each of said elements presents an anterior wall suitable for being applied against said spine and a posterior wall facing away from said anterior wall, and said first portions and said second portions of said elements extend substantially parallel to one another, from said anterior walls to said posterior walls. As a result, as explained in greater detail below in the detailed description of an embodiment of the invention, the first and second portions serve not only to block the elements one against the other, but also make it easier to hold the elastically-compressible means.

Preferably, said bearing second parts of said two elements situated facing each other, and said respective first portions and second portions together define substantially a volume opening out in the anterior and posterior walls of said two elements, said elastically-compressible means extending in said volume. Thus, said elastically-compressible means can be inserted between the elements of the spacer without impediment, when the elements are united together by said link means, either form the posterior walls or from the anterior walls.

Advantageously, said bearing second parts of said elements define respective mean planes, said first portions of said elements extending said bearing second parts substantially parallel to said mean planes, and said second portions of said elements extend said bearing second parts substantially perpendicularly to said mean planes. Thus, said first portion of one of the elements can come into contact with said second portion of the other element which projects from the mean plane of the second bearing portion of the other element while its second portion which projects from the mean plane of its bearing second part is, itself, suitable for coming into contact with said first portion of the other element. As a result, said volume is substantially defined by the facing opposite bearing second parts and by said second portions likewise situated facing each other.

In a particularly advantageous embodiment, said through passage passing through said elements opens out into said first and second portions and extends substantially perpendicularly to said mean planes of said bearing second parts. As a result, the link means of the two elements whose bearing second parts are placed facing each other exert a force that is substantially perpendicular to said mean plane on either side of the bearing second parts, thus enabling traction forces to be shared in balanced manner between the elements of the spacer. This disposition is particularly advantageous when, preferably, the loop-forming continuous link is constituted by a continuous strip of flexible material.

When the link is flexible, it folds easily as soon as the spacer elements are moved towards each other by the spinous processes.

Preferably, said elements of the spacer are made of a rigid material so that they do not deform under the stresses applied by the spinous processes and so as to compress the elastically-compressible means. Advantageously, said elastically-compressible means are formed as a single piece of elastomer. Elastomers constitute a family of elastically-compressible compounds presenting a low hysteresis threshold, which is particularly advantageous for the spacer.

In a particularly advantageous embodiment, each of said first parts of said elements further comprises connection means for connecting said first parts to said spinous processes of said vertebrae. As explained in the detailed description below, these connection means are generally flexible. Nevertheless, rigid means could be used.

BRIEF DESCRIPTION OF THE DRAWINGS

Other features and advantages of the invention will appear on reading the following description of particular embodiments of the invention given by way of non-limiting indication, and with reference to the accompanying drawings, in which.

DETAILED DESCRIPTION OF THE PRESENTLY PREFERRED EMBODIMENTS

Figure 1:
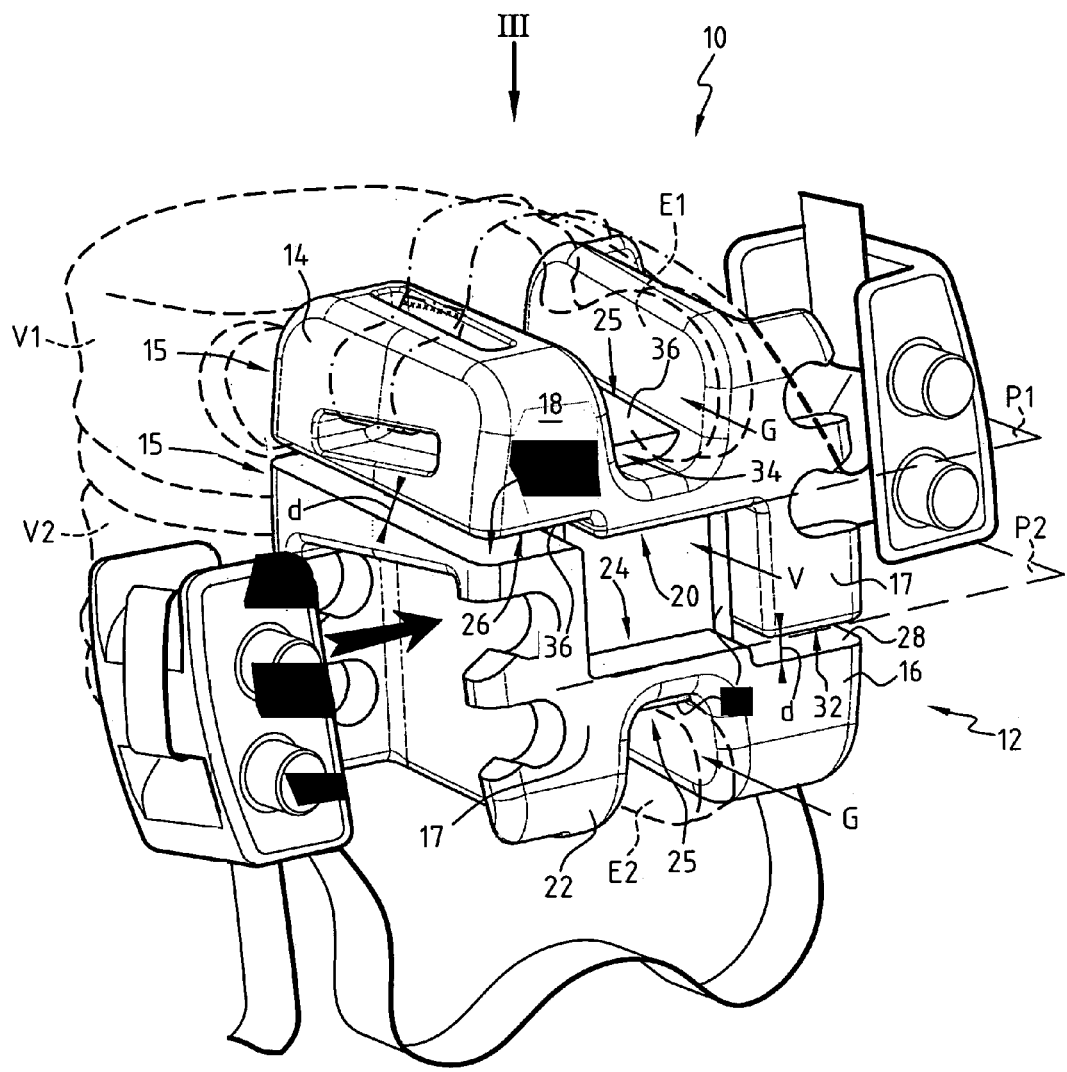
FIG. 1 is a diagrammatic perspective view of an intervertebral implant comprising a spacer in accordance with the invention.

FIG. 1 shows an intervertebral implant 10 including a spacer 12 inserted between two spinous processes E1 and E2 of two respective vertebrae V1 and V2, drawn in fine dashed lines. The spacer 12 comprises two elements 14, 16 whose anterior walls 15 are disposed facing the vertebrae V1 and V2 of the spine, and whose posterior walls 17 face in the opposite direction. The first element 14 presents a first part 18 connected to the spinous process E1 and a second part 20 opposite the first part 18 serving for bearing purposes and defining a mean plane P1. The second element 16 likewise presents a first part 22 which is connected to the spinous process E2 and an opposite-second part 24 for bearing purposes defining a mean plane P2 and situated facing the bearing second part 20 of the first element 14. The first parts 18 and 22 of each element 14 and 16 are formed with a groove G with the spinous processes being engaged between the side walls thereof, which processes bear against the bottoms 25 of the respective grooves G.

In addition, and in symmetrical manner, each element 14, 16 presents a first portion 26, 28 and a second portion 30, 32 situated respectively facing one another in pairs on either side of the bearing second parts 20 and 24. The first portions 26 and 28 extend the edges of the bearing second portions 20 and 24 in slightly set-back manner, substantially parallel to the mean planes P1 and P2, and they extend from the anterior walls 15 to the posterior walls 17. The second portions 30 and 32 of the elements 16 and 14 serve to extend the other edges of the bearing second parts 24 and 20 perpendicularly to the mean planes P2 and P1. In addition, the second portions 30 and 32 also extend from the anterior walls 15 to the posterior walls 17, substantially parallel to the corresponding first portions 28 and 26. Thus, the spacer presents a central volume V, defined by the second parts 20 and 24 of the two elements 14 and 16 situated facing each other and by the respective second portions 32, 30. The volume V opens out into the anterior and posterior walls 15 and 17 of the two element 14 and 16.

In addition, each of the second portions 30 and 32 of the elements 16 and 14 is situated facing respective first portions 26 and 28 of the elements 14 and 16. As explained below, in a rest or first position, the first portions 26 and 28 are respectively spaced apart from each other by a distance d.

Figure 2:
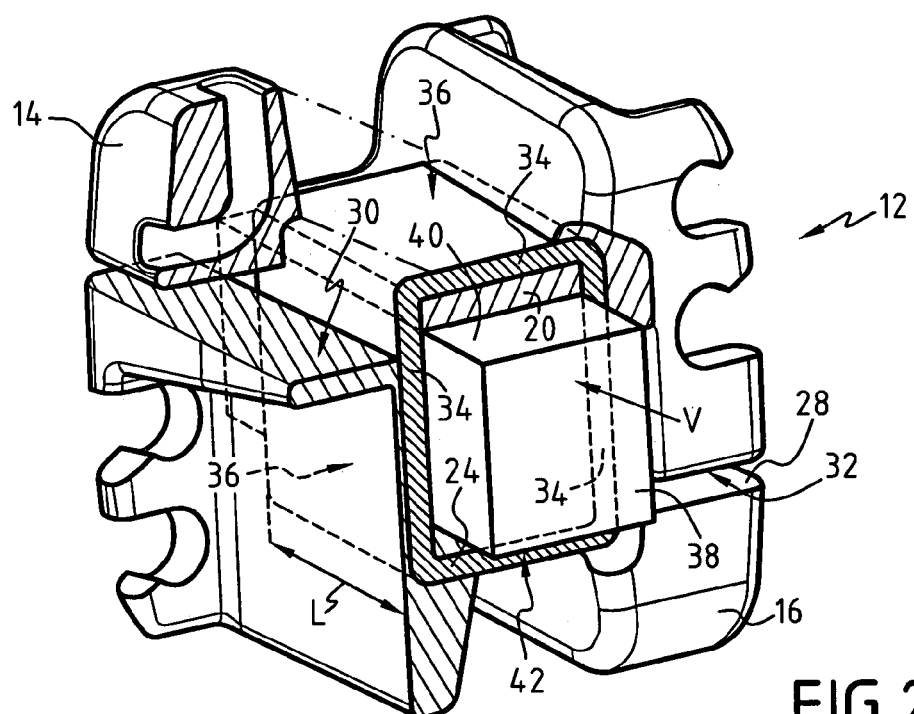
FIG. 2 is a diagrammatic cutaway view of the spacer shown in FIG. 1.
Figure 4:
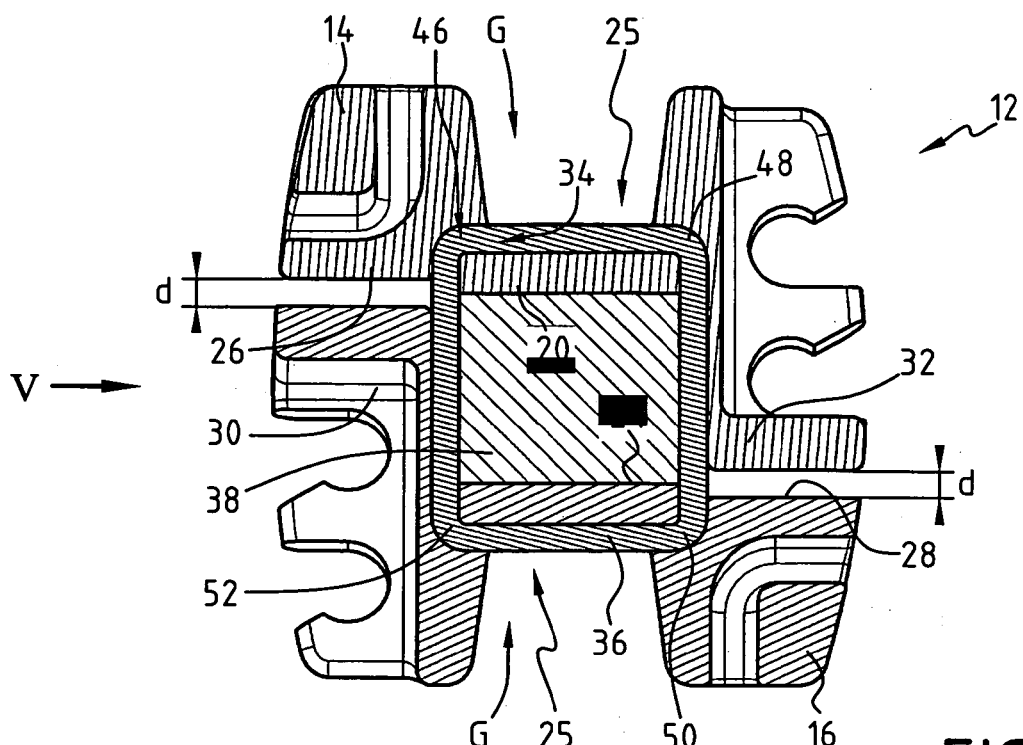
FIG. 4 is a diagrammatic vertical section view of the FIG. 3 spacer on plane IV.

The spacer 12 as shown in FIG. 1 includes link means constituted by a through passage 34 passing through the two elements 14 and 16, and a continuous link 36 forming a loop passing along said through passage 34 so as to interconnect the two elements 14 and 16 of the spacer 12. Reference is made to FIGS. 2 and 4 in order to describe the link means between the two elements 14 and 16 in greater detail, after describing in detail the implant that is shown in a cutaway view in FIG. 2 and which includes elastically-compressible means 38 disposed between the bearing second parts 20 and 24.

In FIG. 2, there can be seen the two elements 14 and 16 whose bearing second parts are placed facing each other, and with the second portions 30 and 32 of the elements 16 and 14 disposed respectively facing the first portions 26 and 28 of the elements 14 and 16.

In addition, there can be seen a substantial fraction of the central volume V which is substantially in the form of a rectangular parallelepiped and in which the elastically-compressible means 38 are contained completely. The elastically-compressible means 38 are constituted by a single substantially rectangular block of biocompatible elastomer material, e.g. of the silicone type. Said block presents a first wall 40 and an opposite second wall 42 that are substantially parallel, the bearing second parts 20 and 24 of the elements 14 and 16 bearing against these first and second walls 40 and 42 of said block. It should be emphasized that the elastically-compressible piece 38 is not positively connected mechanically to the elements 14 and 16. These pieces merely bear against one another.

FIG. 2 also shows the passageway 34 in which the loop-forming continuous link 36 extends in full, for the purpose of holding the elements 14 and 16 together.

The passageway 34 is substantially rectangular in shape of width L that is naturally smaller than the distance between the posterior and anterior walls 17 and 15 so that the first parts 18 and 22 of the elements 14 and 16 are secured to the bearing second portions 20 and 24, respectively.

Reference is made to FIG. 4 in order to describe in greater detail the passageway 34 passing through the two elements 14 and 16, which passageway is followed by the loop-forming continuous link 36.

The passageway 34 passes through the elements 14 and 16 in the same respective portions. It appears in the bottom 25 of the groove G of the element 14 of the spacer 12 and passes through the spacer portions 46 and 48 situated at the bases of the side walls of the groove G, opening out between the bearing second part 20 and the first portion 26 for spacer portion 46, and between the bearing second part 20 and the second portion 32 for spacer portion 48. The passageway is also bordered by the second portion 32 as far as the element 16 where it opens out between the bearing second part 24 and the first portion 28 in the spacer wall 50 in a manner analogous to the spacer portion 46 of the element 14. Thereafter, it passes along the bottom 25 of the groove G so as to open out in spacer portion 52 and extend to the element 14 between the bearing second part 20 and the second portion 32, being bordered by the second portion 30. As a result, the passageway forms a loop going through both elements 14 and 16.

It will be understood that the continuous link 36 which follows said part to form a loop enables the two elements 14 and 16 to be held together.

Figure 3:
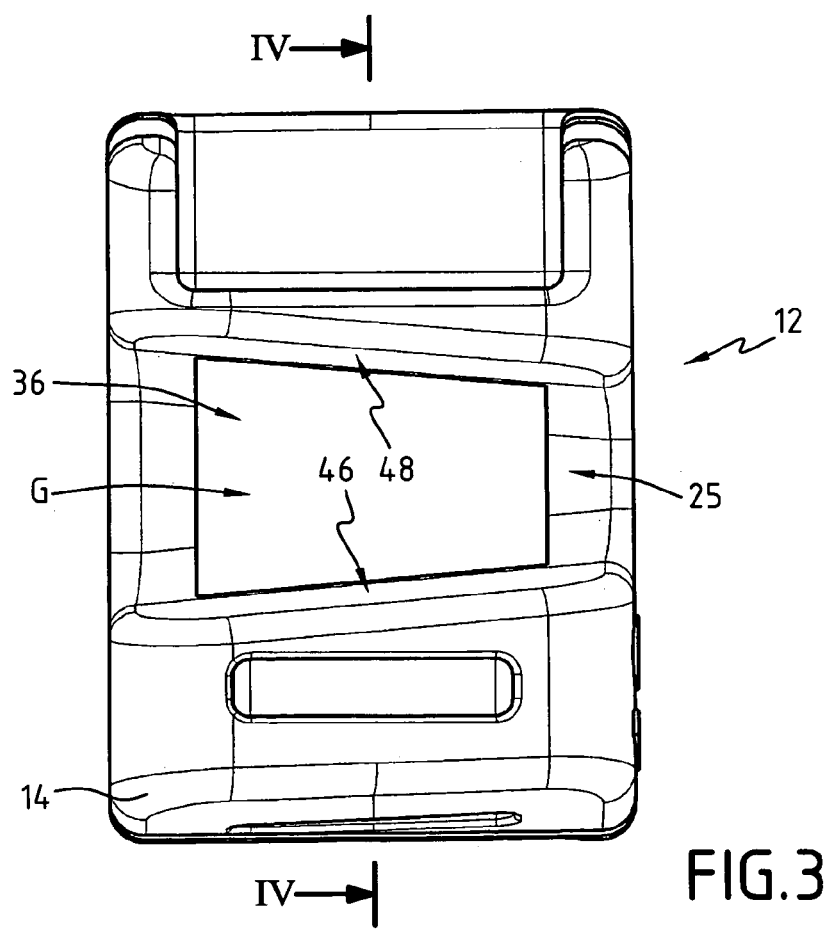
FIG. 3 is a diagrammatic view of the FIG. 1 implant seen from above looking along arrow III.

FIG. 3 shows the spacer 12 seen from above, and in the figure there can be seen the element 14 and the bottom 25 of the groove G along which the continuous link 36 constituting a flexible strip passes. The continuous link 36 engages in the spacer portions 48 and 46 situated at the base of the groove G.

Figure 5:
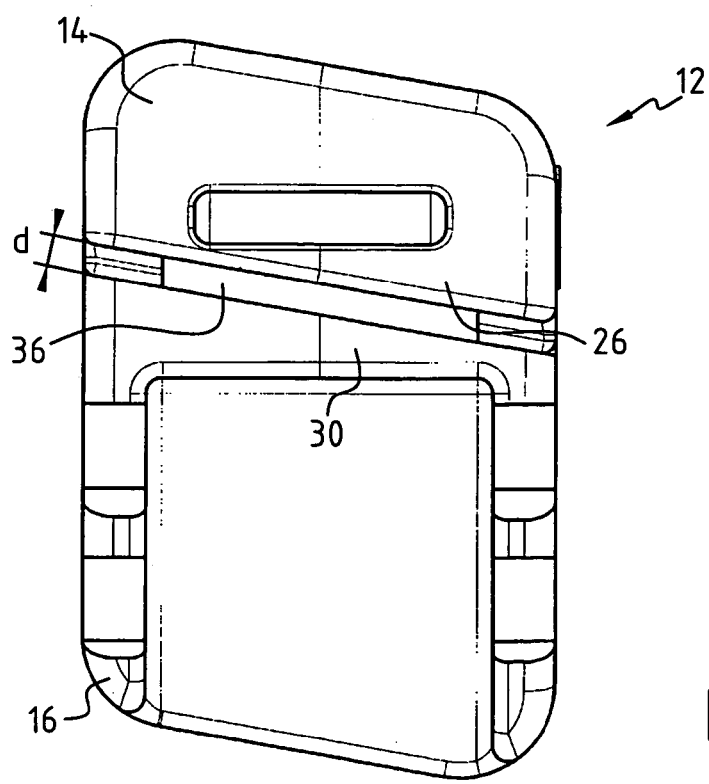
FIG. 5 is a diagrammatic side view of the FIG. 4 spacer seen looking along arrow V.

FIG. 5 shows the spacer 12 in side view, and in the figure there can be seen the element 14 and the element 16, with the continuous link 36 being shown between the first portion 26 and the second portion 30 thereof.

With the essential component elements of the spacer described above, there follows a description of how it is assembled and how it operates.

In a particularly advantageous implementation, the two elements 14 and 16 are pressed against each other so that their first and second portions are respectively in contact. Thereafter the continuous link 36 is put into place by inserting a strip of flexible material around the through passage 34 and by connecting together the two ends of the strip by stitching so as to constitute the continuous link 36. The strip is sewn in the bottom 25 of one of the grooves G which is the only location available to a sewing device.

In addition, the strip is sewn in such a manner that the continuous link 36 is relatively slack while the elements 14 and 16 are disposed one against the other. As a result, as soon as the elements 14 and 16 are driven apart from each other, the continuous link becomes tensioned and the elements 14 and 16 are blocked relative to each other, with the first portions 26, 28 and the second portions 30, 32 being respectively spaced apart from one another by a distance d.

In this position where the elements 14 and 16 are spaced apart from each other, the elastically-compressible means 38 constituted by a single block are inserted by force. As a result, the spacer 12 as shown in FIGS. 2 and 4 is in a rest, first position where the lightly compressed elastically-compressible means 38 exert force in opposite directions on the bearing second parts 20 and 24 of the elements 14 and 16, tending to move them apart from each other. Naturally, the elements 14 and 16 are held together by the continuous link 36.

A spacer 12 is thus obtained in which the elastically-compressible means are prestressed and in which the elements 14 and 16 are capable of being moved towards each other with a determined amount of force until the first and second portions 26, 28 and 30, 32 come respectively into contact with one another, at which point the elements 14 and 16 are blocked one against the other.

Said determined force corresponds to the compressibility of the elastically-compressible means 38. It corresponds to the resistance that is to be applied against moving the spinous processes towards each other, and it is determined by selecting the type of elastomer and by the extent to which it is prestressed.

In addition, since the first parts 18 and 22 of the elements 14 and 16 are rigidly connected to the spinous processes, the extent to which they can move apart from each other is limited solely by putting the continuous link 36 under tension. The bottoms 25 of the grooves G in the two elements 14 and 16 against which the continuous link 36 bears then exerts oppositely-directed forces producing longitudinal tension in the strip constituting said continuous link 36.

The force with which it is desired to hold the spinous processes relative to each other as a function of the stresses to which they are subjected can be determined by selecting a strip made of a material that presents determined elongation under stress.

Thus, the spacer of the invention presents the advantage of being elastically deformable in compression and of being relatively rigid in extension since these two kinds of relative displacement are controlled by two distinct members.

The invention claimed is:

1. An intervertebral implant comprising a spacer for placing between two spinous processes of two vertebrae of the spine, said spacer comprising:
   two elements each presenting a first part provided with a groove configured to receive a spinous process and a bearing second part opposite from said first part, said bearing second parts of said two elements being situated facing each other;
   elastically-compressible means disposed between said bearing second parts, said elastically-compressible means being compressed by said bearing second parts when said two elements are driven towards each other;
   link means distinct from said elastically-compressible means for linking together said two elements, said link means blocking translation movement of said two elements relative to each other when said two elements are driven apart from each other; and
   connection means for connecting the first part of one of said two elements to the spinous process disposed within said groove.

2. An intervertebral implant according to claim 1, wherein said link means comprise at least one passageway passing through each of said elements and opening out substantially on either side of said bearing second part.

3. An intervertebral implant according to claim 1, wherein said link means include a loop-forming continuous link, said continuous link presenting two opposite first portions passing respectively through said two facing elements.

4. An intervertebral implant according to claim 3, wherein said loop-forming continuous link is constituted by a continuous strip of flexible material.

5. An intervertebral implant according to claim 1, wherein each of said elements presents at least a first portion and a second portion situated substantially on either side of said bearing second part said first portion and said second portion of one of said elements pressing respectively against the second portion and the first portion of the other element when said two elements are driven towards each other so as to block them against moving in translation relative to each other, the bearing second parts being suitable for compressing said elastically-compressible means.

6. An intervertebral implant according to claim 5, wherein each of said elements presents an anterior wall applied against said spine and a posterior wall facing away from said anterior wall said first portions and said second portions of said elements extending substantially parallel to one another, from said anterior walls to said posterior walls.

7. An intervertebral implant according to claim 6, wherein said bearing second parts of said two elements situated facing each other, and said respective first portions and second portions together define substantially a volume opening out in said anterior and posterior walls of said two elements, said elastically-compressible means extending in said volume.

8. An intervertebral implant according to claim 5, wherein said bearing second parts of said elements define respective mean planes, and said first portions of said elements extend said bearing second parts substantially parallel to said mean planes, and said second portions of said elements extend said bearing second parts substantially perpendicularly to said mean planes.

9. An intervertebral implant according to claim 8, wherein said through passage passing through said elements opens out into said first and second portions and extends substantially perpendicularly to said mean planes of said bearing second parts.

10. An intervertebral implant according to claim 1, wherein said bearing second parts of said elements define respective mean planes, and said first portions of said elements extend said bearing second parts substantially parallel to said mean planes, and said second portions of said elements extend said bearing second parts substantially perpendicularly to said mean planes.

11. An intervertebral implant according to claim 1, wherein said elements are made of rigid material.

12. An intervertebral implant according to claim 1, wherein each of said first parts of said elements further comprises connection means for connecting said first parts to said spinous processes of said vertebrae.

13. An intervertebral implant comprising a spacer for placing between two spinous processes of two vertebrae of the spine, said spacer comprising:
    two elements each presenting a first part provided with a groove configured to receive a spinous process and a bearing second part opposite from said first part, said bearing second parts of said two elements being situated facing each other;
    elastically-compressible means formed as a single piece of elastomer disposed between said bearing second parts, said elastically-compressible means being compressed by said bearing second parts when said two elements are driven towards each other;
    link means distinct from said elastically-compressible means for linking together said two elements, said link means blocking translation movement of said two elements relative to each other when said two elements are driven apart from each other; and
    connection means for connecting the first part of one of said two elements to the spinous process disposed within said groove.

14. An intervertebral implant according to claim 13, wherein said link means comprise at least one passageway passing through each of said elements and opening out substantially on either side of said bearing second part.

15. An intervertebral implant according to claim 13, wherein said link means include a loop-forming continuous link, said continuous link presenting two opposite first portions passing respectively through said two facing elements.

16. An intervertebral implant according to claim 13, wherein each of said elements presents at least a first portion and a second portion situated substantially on either side of said bearing second part said first portion and said second portion of one of said elements pressing respectively against the second portion and the first portion of the other element when said two elements are driven towards each other so as to block them against moving in translation relative to each other, the bearing second parts being suitable for compressing said elastically-compressible means.

17. An intervertebral implant according to claim 16, wherein each of said elements presents an anterior wall applied against said spine and a posterior wall facing away from said anterior wall said first portions and said second portions of said elements extending substantially parallel to one another, from said anterior walls to said posterior walls.

18. An intervertebral implant according to claim 17, wherein said bearing second parts of said two elements situated facing each other, and said respective first portions and second portions together define substantially a volume opening out in said anterior and posterior walls of said two elements, said elastically-compressible means extending in said volume.

19. An intervertebral implant according to claim 16, wherein said bearing second parts of said elements define respective mean planes, and said first portions of said elements extend said bearing second parts substantially parallel to said mean planes, and said second portions of said elements extend said bearing second parts substantially perpendicularly to said mean planes.

20. An intervertebral implant according to claim 13, wherein said bearing second parts of said elements define respective mean planes, and said first portions of said elements extend said bearing second parts substantially parallel to said mean planes, and said second portions of said elements extend said bearing second parts substantially perpendicularly to said mean planes.

* * * * *